United States Patent [19]

Chen et al.

[11] Patent Number: 5,599,173
[45] Date of Patent: Feb. 4, 1997

[54] BLOOD PUMP SYSTEM

[75] Inventors: Herbert Chen, Kensington; Ronald A. Ness, Castro Valley; John C. Woodard, Walnut, all of Calif.

[73] Assignee: Baxter International, Inc., Deerfield, Ill.

[21] Appl. No.: 473,220

[22] Filed: Jun. 7, 1995

Related U.S. Application Data

[63] Continuation of Ser. No. 194,481, Feb. 10, 1994, Pat. No. 5,511,958.
[51] Int. Cl.$^6$ .......................... F04B 43/00; F01B 19/00; A61M 1/10
[52] U.S. Cl. .................. 417/412; 417/413.1; 417/478; 417/479; 128/DIG. 3; 623/3; 277/105; 277/110; 285/351; 285/353; 285/354
[58] Field of Search ................................ 417/412, 413, 417/478, 479; 128/DIG. 3; 600/16–18; 623/3; 277/102, 105, 110; 285/351, 353, 354

[56] References Cited

U.S. PATENT DOCUMENTS

| 3,011,803 | 12/1961 | Buckner et al. | 285/351 |
|---|---|---|---|
| 4,557,673 | 12/1985 | Chen et al. | 417/412 |
| 4,578,077 | 3/1986 | Joh | 623/3 |
| 5,041,131 | 8/1991 | Nagase | 623/3 |
| 5,171,207 | 12/1992 | Whalen | 600/16 |

FOREIGN PATENT DOCUMENTS 0449272  6/1936  United Kingdom .................. 285/353

OTHER PUBLICATIONS

Pierce, et al., "Complete Left Ventricular Bypass With a Paracorporeal Pump: Design and Evaluation", vol. 180, No. 4, Annals of Surgery, Oct. 1974, 418–426.

*Primary Examiner*—Edward K. Look
*Assistant Examiner*—Christopher Verdier
*Attorney, Agent, or Firm*—Coudert Brothers

[57] ABSTRACT

A pump system is described which is particularly suited for use as a left ventricular assist device for internal use in humans. The pump system generally includes a pump having a deformable sac formed in a seamless piece of flexible resilient material having (i) a pair of opposite substantially planar walls and of substantially circular shape joined by an annular wall of substantially semicircular cross-section and (ii) inlet and outlet means. The inlet means have an asymmetric tapered section positioned to direct the inlet flow toward the annular wall of the sac to produce a smooth circular flow within the sac and minimize thrombus formation. A pair of pusher plates are disposed on opposite sides of the sac. Each of the pusher plates are engageable with a respective one of the planar walls of the sac for displacing at least one of the planar walls toward the other to deform the sac. The pump system also includes removable inlet and outlet conduit means with valve means for controlling inlet and outlet flow. Each of the conduit means include connecting means having sealing means for securing the inlet and outlet conduit means to the pump.

3 Claims, 8 Drawing Sheets

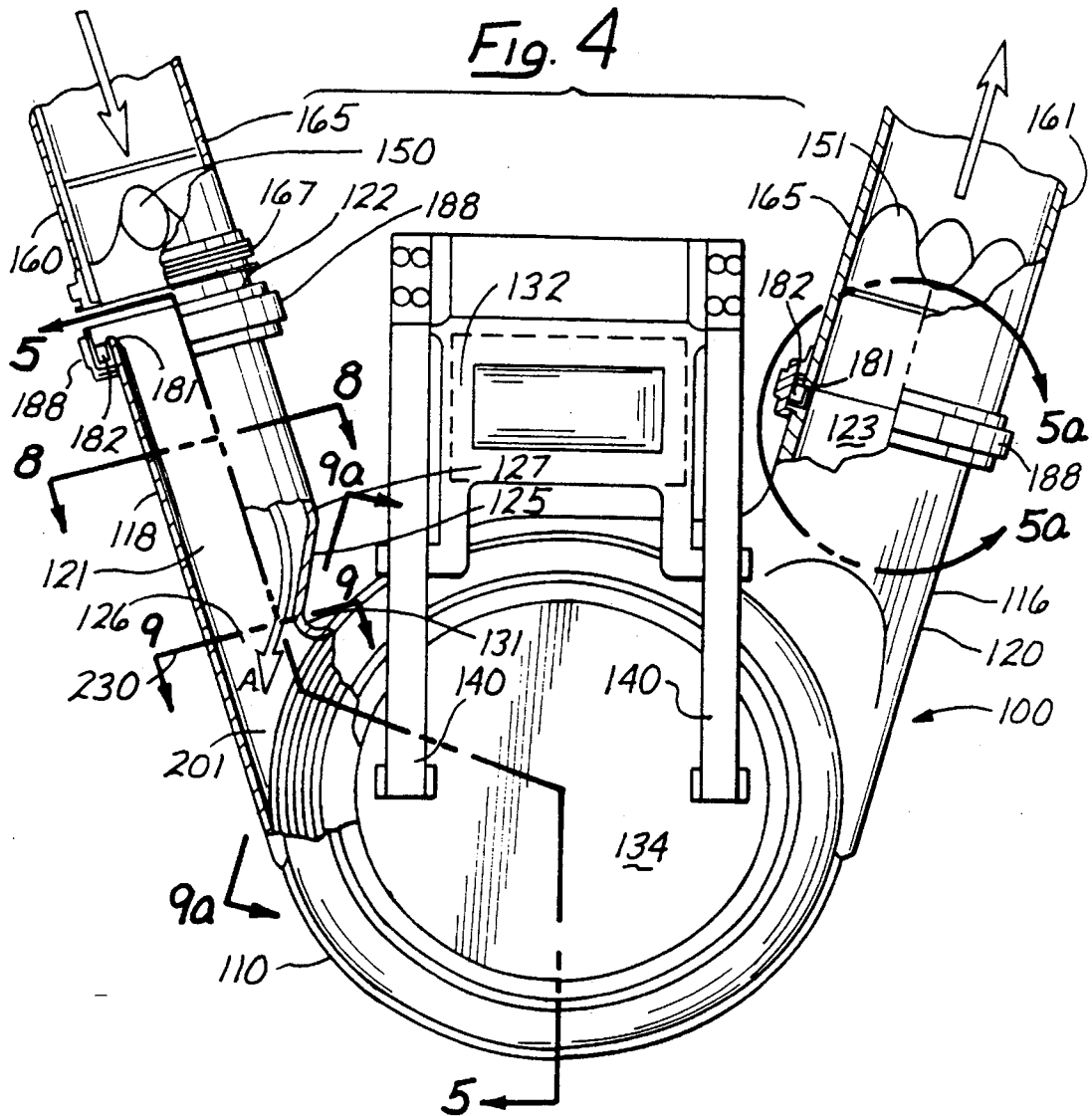
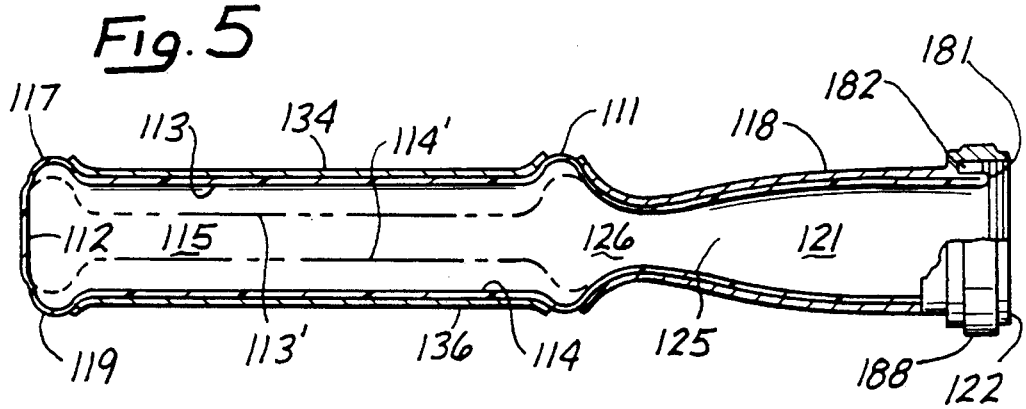

５,599,173

BLOOD PUMP SYSTEM

This is a continuation, of application Ser. No. 08/194,481 filed Feb. 10, 1994, now U.S. Pat. No. 5,511,958.

FIELD OF THE INVENTION

This invention relates generally to blood pump systems for internal use in humans. More particularly, the invention relates to a blood pump system which is particularly suited for use as a left ventricular assist device.

BACKGROUND OF THE INVENTION

Efforts to develop an artificial heart have produced a wide variety of blood pump configurations and/or systems. This particular invention relates to "sac type" pumps in which a deformable sac is utilized to provide the pumping action. Deformation of the sac to reduce its internal volume causes the expelling of the sac contents or a portion thereof through a one way valve. Return of the sac to its original undeformed condition expands its internal volume and causes inflow of fluid into the sac through a one way valve for the next pumping stroke. These types of pumps are analogous to the action of the heart in humans and animals.

Devices of the aforementioned type may be actuated in a variety of ways. Some devices employ pneumatic actuation. Others employ expanding or contracting fluids. Still others employ electrical devices such as solenoids or motors for actuation.

With any type of blood pump system (or device) to be implanted in a human, however, a number of common problems are presented. First of all, the system must be suitable for implantation in that its size and configuration must be such as to be readily accommodated in some body cavity. Inlet and outlet connections to the system should be such as to facilitate connection of the system into the bloodstream to provide the desired pumping action. The inlet and outlet connections must also be relatively simple and reliable. The system must also be highly reliable for long periods of time of continuous use. Finally, flow characteristics of the system should be such as to prevent thrombus formation or clotting in the blood.

Although prior art blood pump devices and/or systems have provided promise in certain respects, most have had sufficiently significant defects as to prevent their successful use. Among these defects has been the presence of a diaphragm-housing junction or discontinuity which frequently results in thrombus formation. Other factors contributing to thrombus formation have been poor internal geometry, poor material choice, and wrinkling during deformation of the sac.

U.S. Pat. No. 4,557,673 (assigned to Novacor Medical Corporation, Oakland, Calif.) discloses a deformable sac blood pump system which substantially reduces or eliminates many of the disadvantages and shortcomings associated with previously developed deformable sac systems. As discussed in detail below, the noted pump system's superior performance is primarily due to (i) the circular pump chamber shape, (ii) the tangential placement of the inflow and outflow ports, and (iii) stable pump sac deformation. These factors result in rapid development of a circular flow or "wash" pattern within the pump chamber during the filling phase (especially at low stroke volumes) which minimizes the likelihood of thrombus formation.

Referring to FIGS. 1–3, the blood pump system of the noted patent comprises a pump 10 having a chamber structure which is generally shown at 12. Structure 12 includes a deformable sac 14 having an annular sidewall 16 and a pair of opposed circular, movable walls 18, 20 (see FIG. 2) joined to the sidewall through flexible convoluted (or curved) wall portions 22, 24, respectively. Fluid is supplied to the sac chamber or annulus 26 through an elongated inlet port 28 and is expelled under pressure through an elongated outlet port 30.

In the noted blood pump 10, the inlet and outlet ports 28, 30 have a substantially circular cross-section throughout their respective lengths and are arranged to direct inlet and outlet flow substantially tangentially with respect to the annular side wall of the sac. The ports 28, 30 are provided with valve means, such as inlet valve 32, to produce the requisite one direction flow valving in the pump. As illustrated in FIG. 2, the inlet valve 32 is disposed in the chamber structure 12 in close proximity to the sac annulus 26 to quickly establish a circular flow pattern that effectively washes the sac annulus 26 and inlet valve 32.

A pair of opposed pusher plates 34, 36 are attached to pump actuator 38 to produce expulsion of fluid from the sac annulus 26. The actuator 38 is mechanically connected to each pusher plate 34, 36 through connecting arms, such as arm 40 connecting the actuator to plate 34.

Completing the description of what is generally shown in FIG. 1, pump 10 has a housing 42 which includes a rigid housing ring 44 and a rigid shell 46 encasing the central region of structure 12. The shell 46 is formed with passages which accommodate the inlet and outlet ports 28, 30 in the sac 14.

An object of the present invention to provide a deformable sac blood pump system which incorporates many of the advantageous features disclosed in the above noted patent, and which provides a number of unique and hitherto unknown features which enhance the system's operational characteristics.

A more specific object of the invention is to provide in such a pump system removable inlet and outlet conduits having valves therein to control the flow into and out of the deformable sac.

A related object of the invention is to provide such a pump system in which the number of interposed biomaterial and step transitions at the interfaces between the valved conduits and pump are minimized.

Another object of the invention is to provide in such a pump system a deformable sac having an inlet port with a tapered section to direct the inlet flow toward the annular wall of the sac during pumping operation, resulting in a uniform flow action which minimizes the likelihood of thrombus formation on inner sac surfaces.

A further object of the invention is to provide such a pump system which rapidly develops a uniform flow pattern within the sac chamber, while maintaining low filling and ejection pressures.

Yet another object of the invention is to provide such a pump system which accommodates a broad range of stroke volumes.

SUMMARY OF THE INVENTION

The blood pump system generally includes a deformable sac formed in a seamless piece of flexible resilient material having (i) a pair of opposite substantially planar walls and of substantially circular shape joined by an annular wall of substantially semicircular cross-section and (ii) inlet and outlet means. The inlet means have an asymmetric tapered section positioned to direct the inlet flow toward the annular wall of the sac to produce a smooth circular flow within the sac and minimize thrombus formation. A pair of pusher plates are disposed on opposite sides of the sac. Each of the pusher plates are engageable with a respective one of the planar walls of the sac for displacing the planar walls toward each other to deform the sac. Displacement means are also provided for periodically displacing both of the plates simultaneously toward each other. The pump system also includes removable inlet and outlet conduit means with valve means for controlling inlet and outlet flow. Each of the conduit means include connecting means with sealing means for securing the inlet and outlet conduit means to the pump.

BRIEF DESCRIPTION OF THE DRAWINGS

Further features and advantages will become apparent from the following and more particular description of the preferred embodiment of the invention, as illustrated in the accompanying drawings, in which like referenced characters generally refer to the same parts or elements throughout the views, and in which:

FIG. 4 is a plan view of a blood pump system in accordance with the invention;

FIG. 5 is a sectional view taken generally along line 5—5 in FIG. 4;

DETAILED DESCRIPTION OF THE INVENTION

In accordance with the present invention, the blood pump system generally includes a deformable sac having, in the non-deformed configuration, a pair of opposite substantially planar walls of substantially circular shape joined by an annular wall of substantially semicircular cross-section and inlet and outlet means, a pair of pusher plates for displacing the planar walls toward each other to deform the sac and removable inlet and outlet conduits having valves therein.

As discussed in detail below, the inlet means of the invention comprises a port having an asymmetric tapered section to direct the inlet flow toward the annular wall of the sac. During pumping operation it was found that tapered inlet means produced an optimum circular flow pattern within the sac, minimizing the likelihood of thrombus formation on inner sac surfaces.

Figure 1:
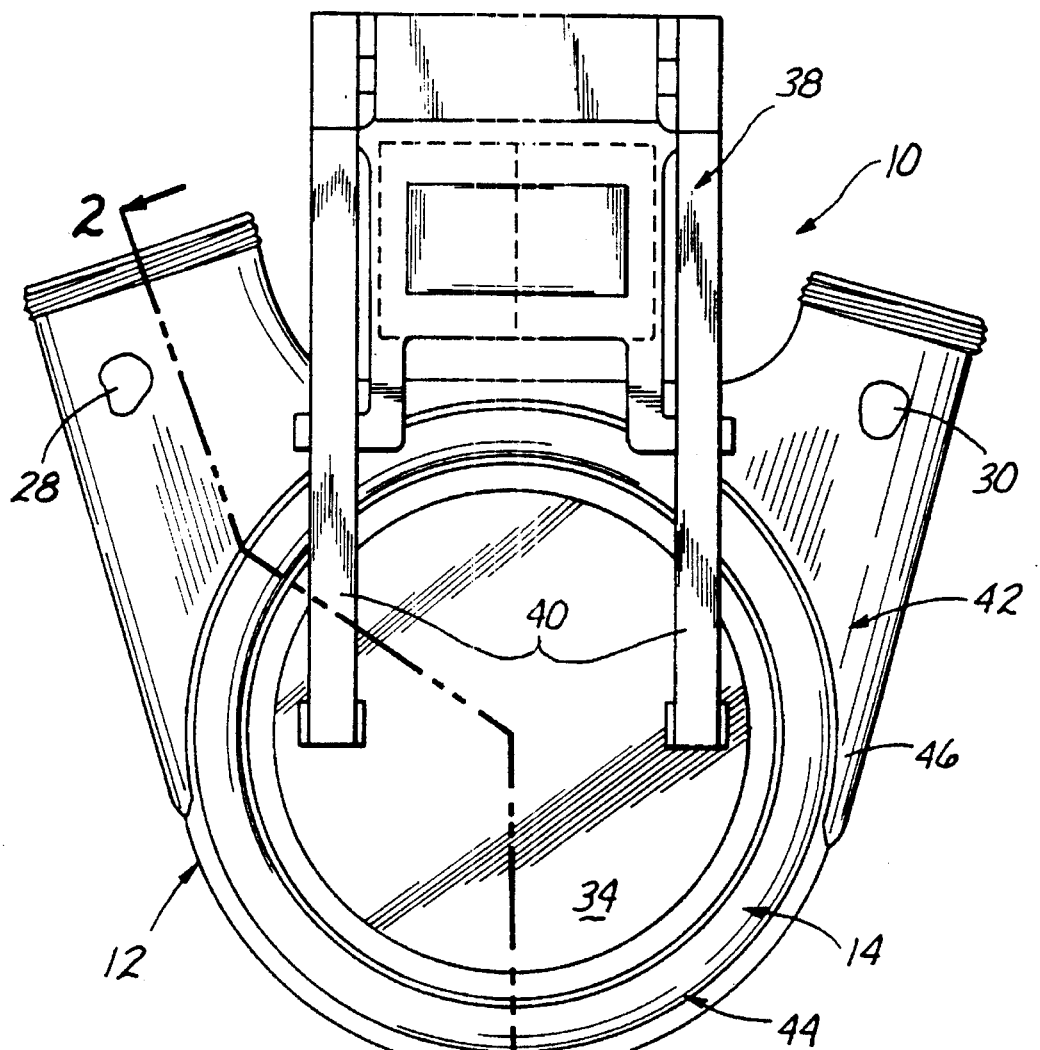
FIG. 1 is a plan view of a prior art blood pump system.
Figure 2:
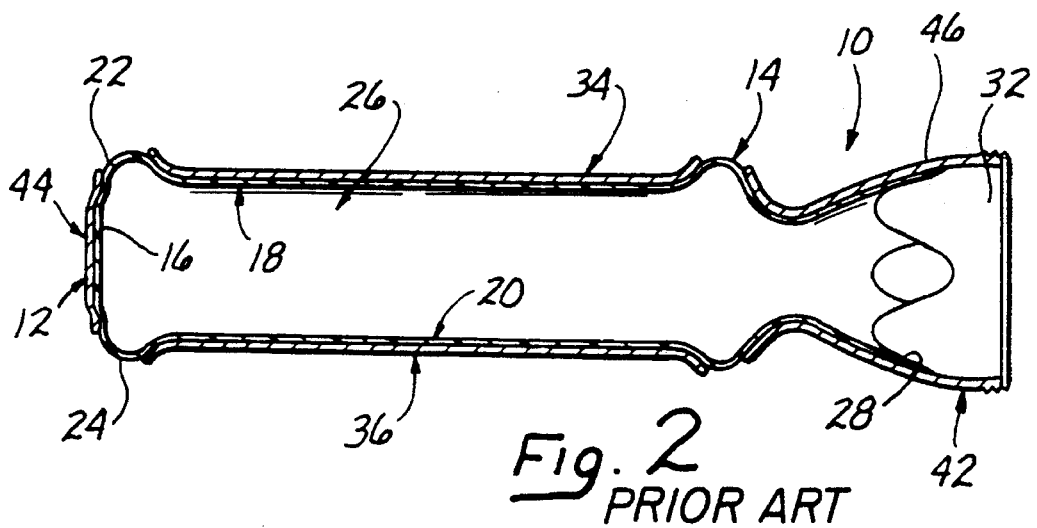
FIG. 2 is a sectional view taken generally along line 2—2 in FIG. 1.
Figure 3:
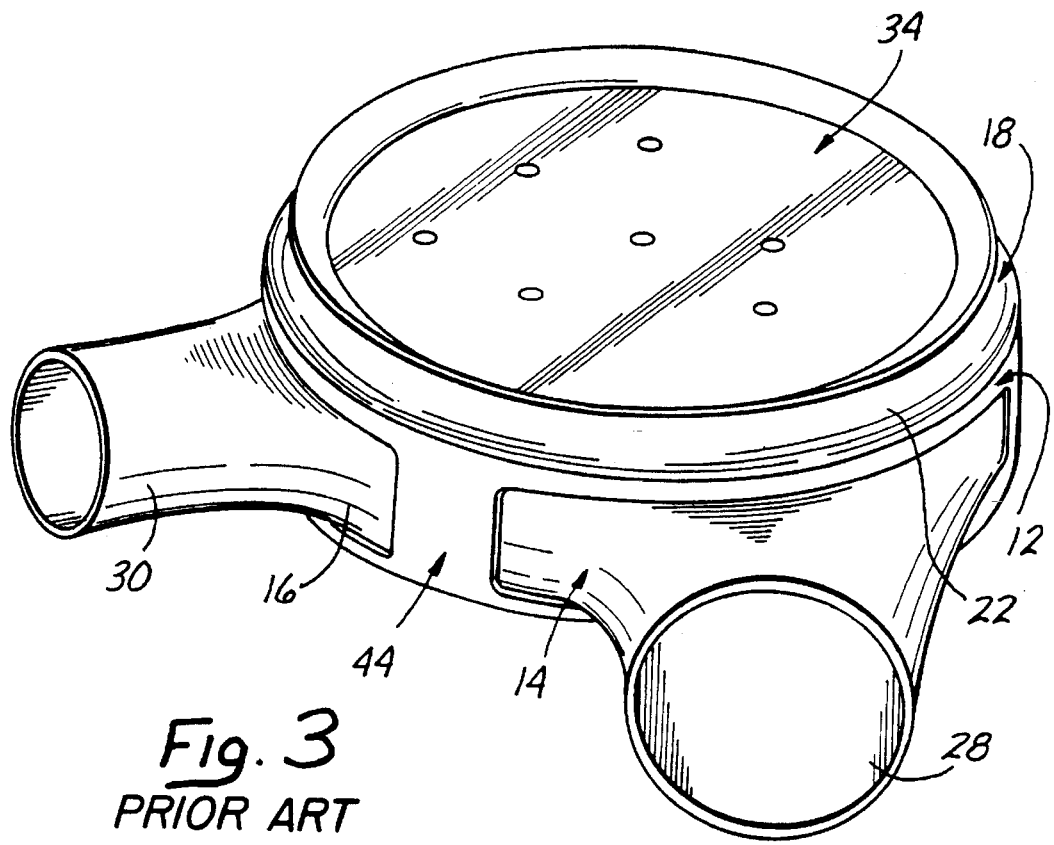
FIG. 3 is a perspective view of a prior art blood pump sac.
Figure 5A:
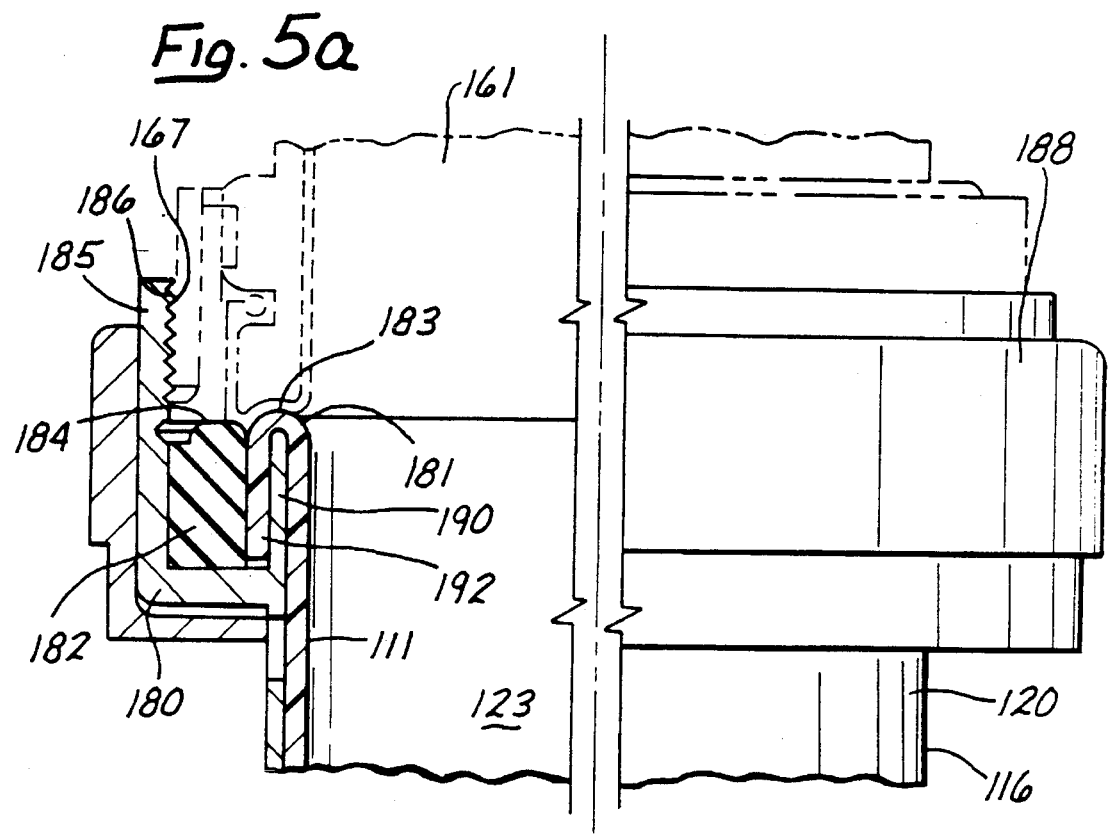
FIG. 5a is a sectional view taken generally along arc 5a—5a in FIG. 4.
Figure 6:
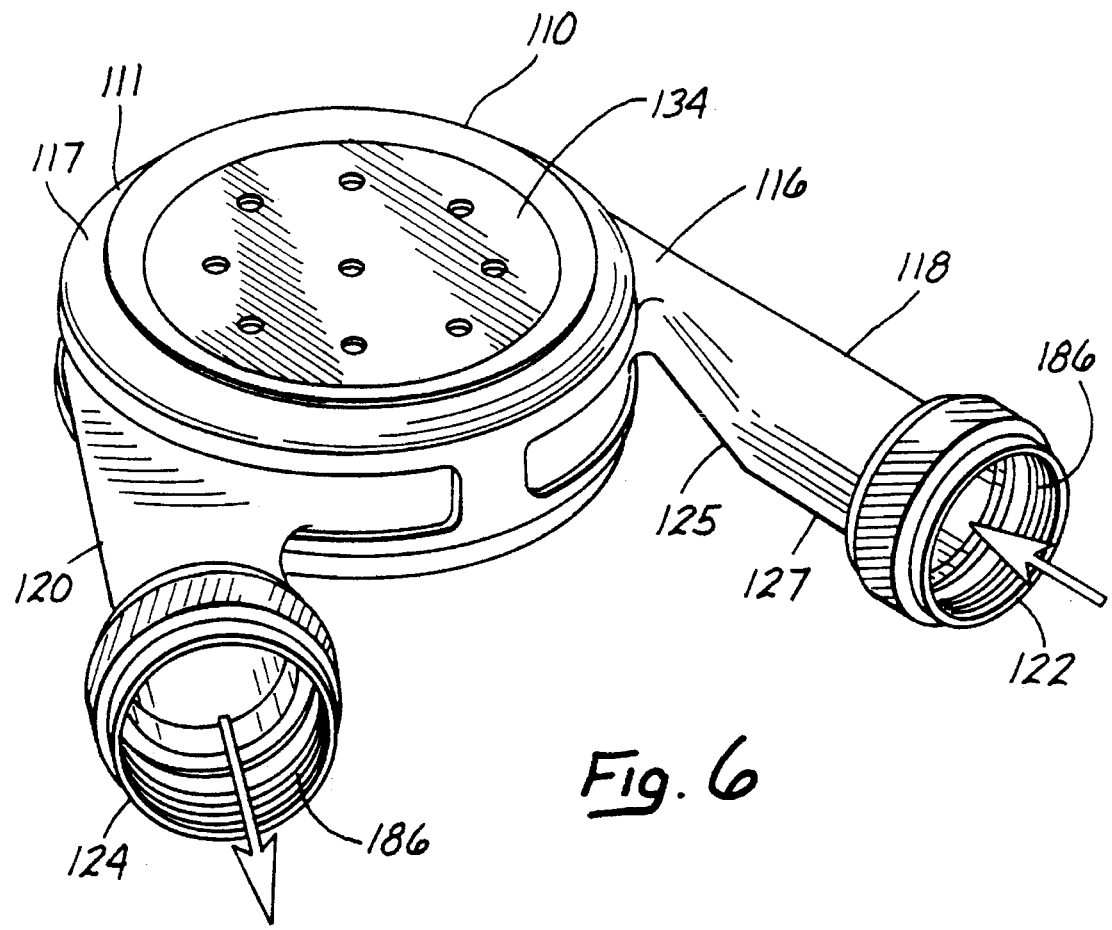
FIG. 6 is an isometric view of a blood pump system illustrating the undeformed sac and pump housing geometry in accordance with the invention.

Referring to FIG. 4, the blood pump system of the invention includes a pump 100 having a chamber structure which is generally shown at 110 and whose components are shown removed from other parts of the pump 100 in FIG. 6. The chamber structure 110, whose construction and unique features will be described in greater detail below, includes a deformable sac 111 having an annular sidewall 112, a pair of opposed circular, movable walls 113, 114 joined to the sidewall through flexible curved wall portions 117, 119, respectively. These parts define a variable volume annular sac chamber, or annulus 115 (see FIG. 5). Fluid is supplied to the annulus 115 through the inlet port 121 and is expelled under pressure through an outlet port 123.

As illustrated in FIG. 4, the deformable sac 111 is contained within a housing 116 of rigid material formed generally in the same shape as that of the sac 111. The housing 116 is formed with passages 118 and 120 which accommodate the inlet and outlet ports 121, 123 respectively, of the sac 111. In further embodiments, the entire pump structure 110 may additionally be encased in a fluid-tight outer housing which is coated with a suitable biocompatible material.

The blood pump 100 also includes a pair of opposed pusher plates 134, 136 which engage the planar walls 113, 114. In the preferred embodiment, the pusher plates 134, 136 are movable inwardly under the control of displacement means and, hence, move planar walls 113, 114 inwardly to an "end-of-stroke" position 113', 114', producing expulsion of fluid from the sac annulus 115. As will be recognized by one skilled in the art, the pump 100 may be constructed so that only one of the pusher plates moves toward the other to displace the associated planar wall and reduce the volume of the pump chamber.

The displacement means is mechanically connected to each pusher plate 134, 136 through connecting arms, such as arm 140 connecting the displacement means to plate 134. The displacement means function to close opposed connecting arms coordinatedly to produce the desired pumping action in the pump.

The displacement means of the invention may include pneumatic actuation, expanding or contracting fluids or electrically powered motors or solenoid type actuators. Preferably, the displacement means comprises a solenoid actuator 132 which is of high efficiency, electrically controlled, and pulsed. Use of a solenoid having an armature which is decoupled from the blood pump mechanical drive by means of an intermediate energy storage spring provides high efficiency, low inertia, and high responsiveness at cardiac rates. Moreover, the inherent simplicity of a solenoid drive offers long-term reliability.

As illustrated in FIGS. 5 and 6, the inlet and outlet means 122, 124 communicate with the sac annulus 115 through elongated inlet and outlet ports 121, 123, respectively. Each port 121, 123 is substantially coextensive, in an arcuate direction, with a corresponding inlet and outlet housing 118, 120, respectively, through which that part of the sac 111 extends. An advantage of this construction is that the fluid passage area of the inlet and outlet ports 121, 123 is formed in an anchored, stationary sidewall portion of the sac 111, whereby the shape of ports 121, 123 is substantially constant during pump operation.

The sac 111 of the present invention is formed in a seamless piece of flexible resilient, blood compatible material. According to the invention, the sac material may be of any type suitable for pumping blood. The material of which the sac 111 is comprised should have long term retention of physical strength under combined dynamic stressing and hydrolysis. The material should be of low toxicity and long term chemical stability for compatibility with blood. The sac material should also be (i) high strength, (ii) capable of being repeatedly flexed, (iii) capable of being sterilized, and (iv) easily fabricated.

As will be recognized by one skilled in the art, various biocompatible sac materials may be employed within the scope of the invention. In the preferred embodiment, the sac material comprises a linear segmented polyurethane.

The internal surface of the sac 111 should also avoid thrombus formation. According to the invention, the preferred blood contacting surface is a smooth polyurethane antithrombogenic surface. However, as will be recognized by one skilled in the art, various blood contacting surfaces and/or surface coatings may be employed within the scope of the invention.

As previously stated, the inlet and outlet means 122, 124 of the invention comprise elongated inlet and outlet ports 121, 123 which are formed in a unitary piece with the sac 111. In the preferred embodiment, the ports 121, 123 extend tangentially of the annulus formed by the annular wall 112 of the sac 111. This is for the purpose of directing the blood flow tangentially into and out of the interior of the sac 111 to minimize discontinuities in the flow and reduce the likelihood of thrombus formation.

As will be recognized by one skilled in the art, the internal and/or opening dimensions of the inlet and outlet ports 121, 123 are critical. As previously stated, a primary objective of the invention is to rapidly develop a uniform circular flow or wash pattern within the sac 111 at both high and low stroke volumes, while maintaining low filling and ejection pressures. To meet this objective a variety of conflicting requirements must be satisfied.

For example, for a given inlet opening (or throat) area and a given filling pressure, a higher stroke volume will establish a good flow pattern in the sac annulus 115 faster than a smaller stroke volume. At lower stroke volumes there will be a lower inflow rate and, hence, lower filling velocity. Up to a point, the filling velocity for low stroke volumes can be increased by decreasing the inlet throat area, resulting in a more vigorous sac annulus 115 flow pattern. Beyond that point, a decrease in throat area increases the filling resistance, resulting in lower inflow rate and velocity. The lower inflow rate and velocity will cause a degradation in the flow pattern, increasing the likelihood of thrombus formation.

With regard to the outlet opening area, a small throat will produce a more vigorous, uniform flow pattern during the filling phase. In contrast, a large outlet opening causes a flow discontinuity that disrupts the circular flow pattern within the sac annulus 115. However, two factors limit the downsizing of the outlet opening—increased ejection resistance and sac manufacturability, discussed below.

One preferred method of sac manufacture comprises successively coating an accurately machined and polished aluminum mandrel whose outer surfaces define the inner surfaces of the sac 111. Since both of the opposed annular flexible portions of the sac 113, 114 are circumferentially uniform, the surfaces of the mandrel forming such flexible surfaces can be accurately machined, polished, and coated to produce extremely regular and smooth surfaces. To form the sac 111, the coated mandrel is repeatedly dipped in a selected polymer solution and dried while rotated under infrared lamps.

To remove the sac 111 from the mandrel, the mandrel must be extricated through either the inlet 121 or outlet 123 port. Thus, the mandrel size and shape directly impacts the internal configuration and minimum dimensions of the port through which the mandrel is extricated.

As discussed in detail below, the blood pump system of the invention reflects an optimum resolution of the above noted conflicting parameters. The inlet port configuration is optimized to provide excellent flow patterns and physiologically acceptable fill resistance over a wide range of stroke volumes. The outlet port configuration is similarly optimized to provide a uniform, vigorous flow pattern within the sac annulus 115. The outlet port configuration also facilitates removal of the sac 111 from the mandrel during the above described dip-cast process.

Figure 7:
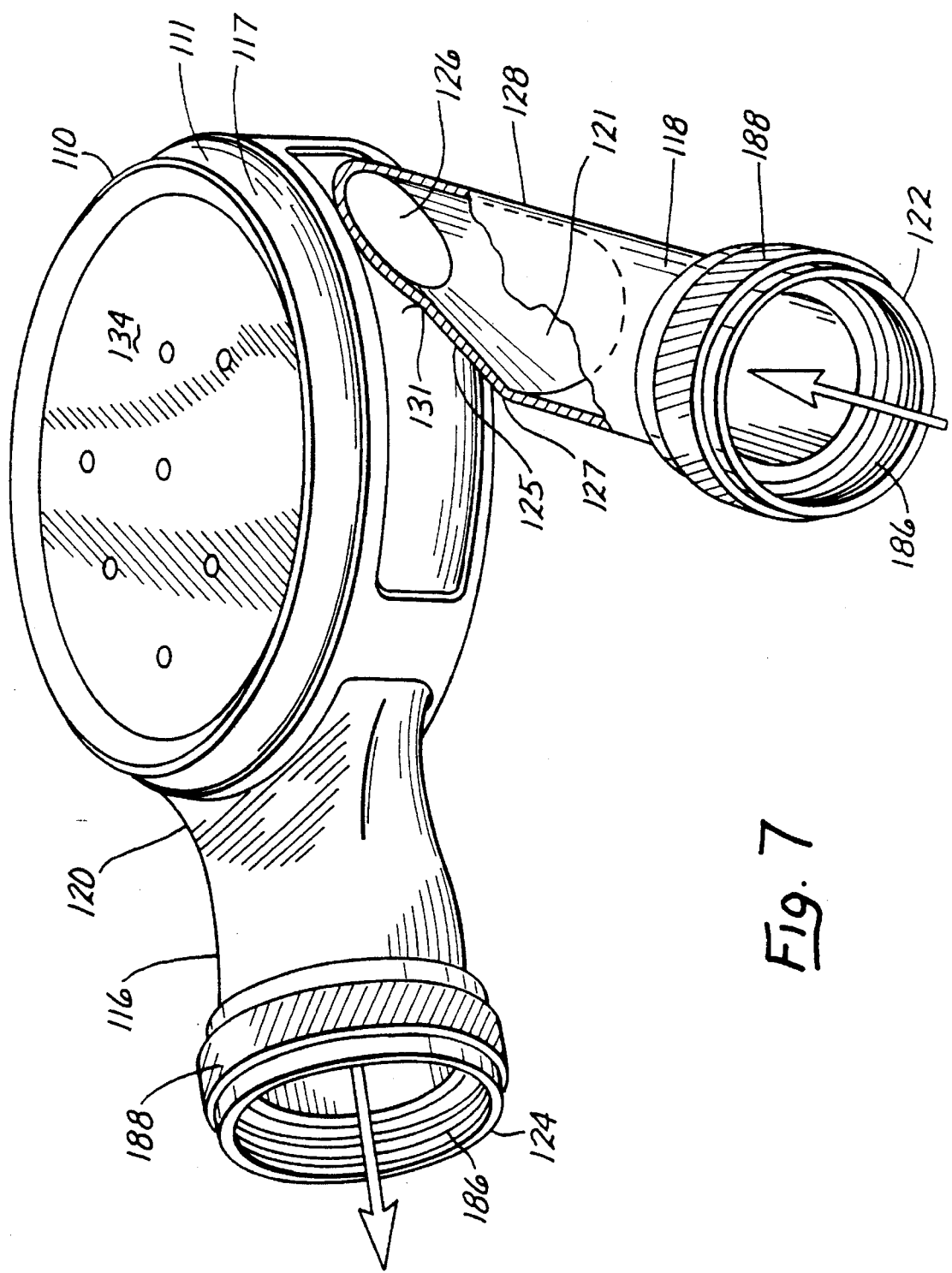
FIG. 7 is an isometric partial section view of a blood pump system illustrating the tapered inlet port configuration in accordance with the invention.

Details of the inlet port 121 will now be considered with particular reference to FIGS. 4–9. Referring first to FIGS. 4 and 7, in the preferred embodiment of the invention, the inlet port 121 includes an asymmetric frustoconical tapered section 125 positioned to direct the incoming blood toward the annular wall 112 of the sac 111 (see Arrow A). It has been found that the asymmetric frustoconical tapered section with a substantially elliptical throat (discussed below), produces an optimum circular flow pattern within the sac annulus 115. The tapered section 125 is also sufficiently uniform to prevent thrombus formation.

Figure 9A:
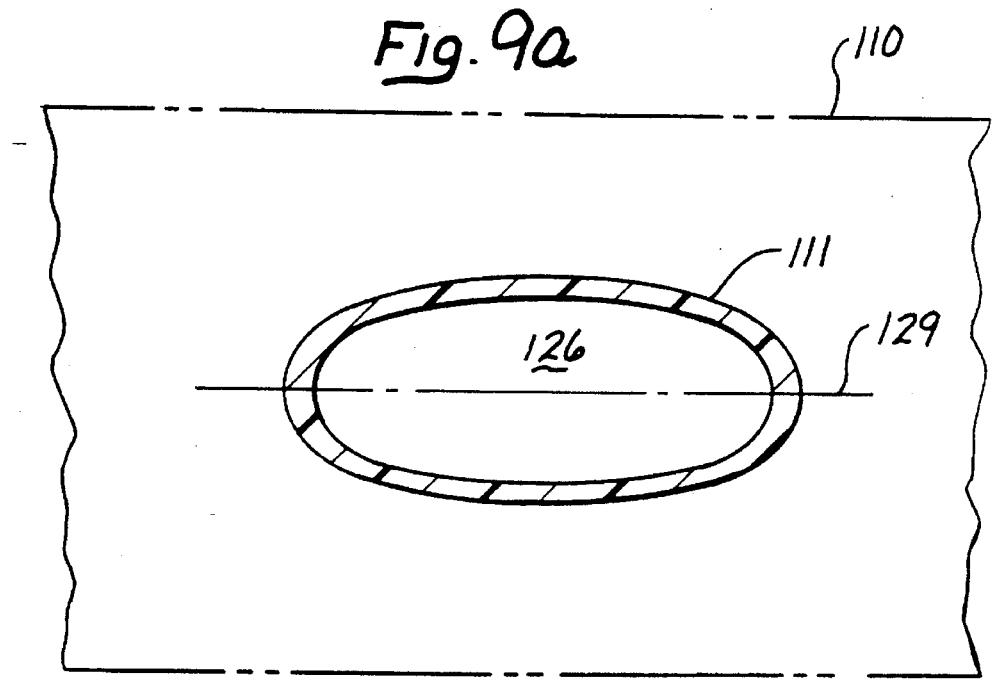
FIG. 9a is a sectional view taken generally along line 9a—9a in FIG. 4.
Figure 8:
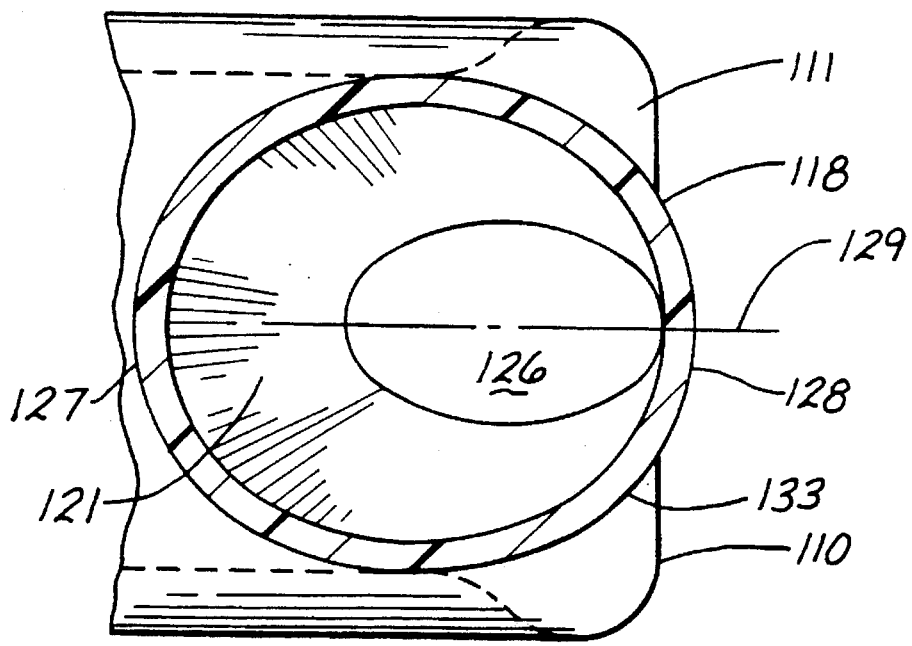
FIG. 8 is a sectional view taken generally along line 8—8 in FIG. 4.
Figure 9:
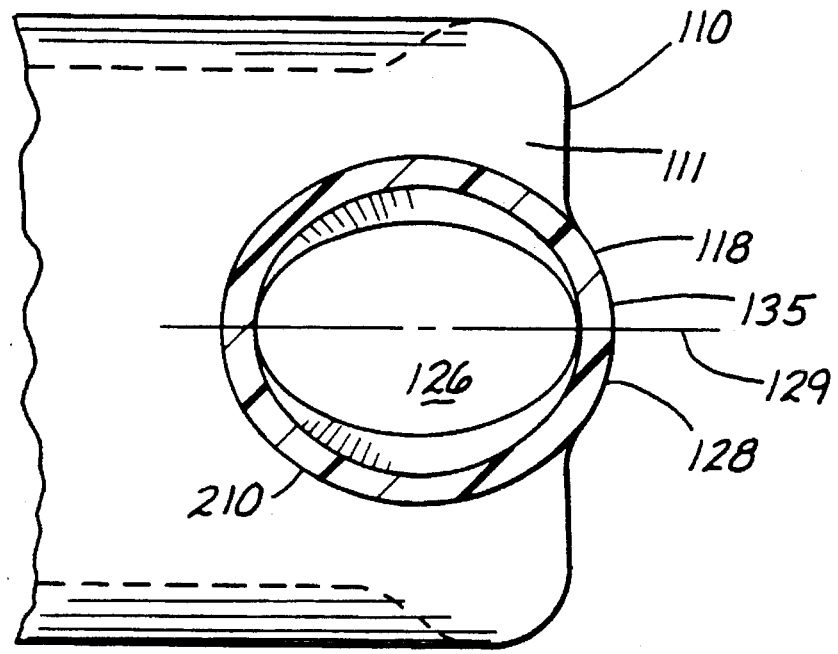
FIG. 9 is a sectional view taken generally along line 9—9 in FIG. 4.

As illustrated in FIG. 8, the asymmetric tapered section 125 has a substantially circular inlet 133 on one end and a substantially elliptically shaped throat 126 on the opposite end. In the preferred embodiment, the outer wall of the throat 135 is contiguous with the outer wall of the inlet port 128 to direct inlet flow substantially tangentially with respect to the annulus defined by the annular wall 112 of the sac 111 (see FIG. 9). As further illustrated in FIGS. 8 and 9a, the elongated axis 129 of the throat 126 substantially lies in a plane that is contiguous with the mid-plane of the circular cross-section of the deformable sac 111.

As stated, the above described asymmetric tapered section 125 results in a uniform, preferably circular, flow pattern within the sac 111, minimizing thrombus formation. The tapered section 125 also helps to reduce flow separation at the junction 131 between the inlet port 121 and sac annulus 115.

In the preferred embodiment of the invention, the substantially circular inlet port 121 (and taper inlet 133) has a diameter in the range of approximately 18 to 33 mm, preferably 20 to 22 mm. As illustrated in FIGS. 4 and 8, the tapered section 125 initially converges to a substantially circular section 210 (see FIG. 9) having a diameter in the range of approximately 12 to 17 mm, preferably 14 to 16 mm. As the tapered section 125 blends into the substantially circular chamber structure 110, the tapered section 125 converts to a generally elliptical shaped section. The elliptically shaped throat 126 of the tapered section 125 has a height (in plane 9—9, denoted 230) of approximately 10 to 15 mm, preferably 11 to 13 mm.

The length of the tapered section 125 is generally in the range of approximately 15 to 23 mm, preferably 17 to 22 mm. The angle of the tapered section 125 with respect to the inner wall 127 of the inlet port 121 is generally in the range of approximately 15° to 30°, preferably 17° to 28°, more preferably 26°.

According to the invention, the tapered section 125 reduction in cross-sectional area per unit length may be linear, nonlinear or a combination thereof. In the preferred embodiment (discussed in detail below), the reduction in cross-sectional area per unit length of the tapered section 125 is initially linear, converting to a non-linear section.

Figure 10:
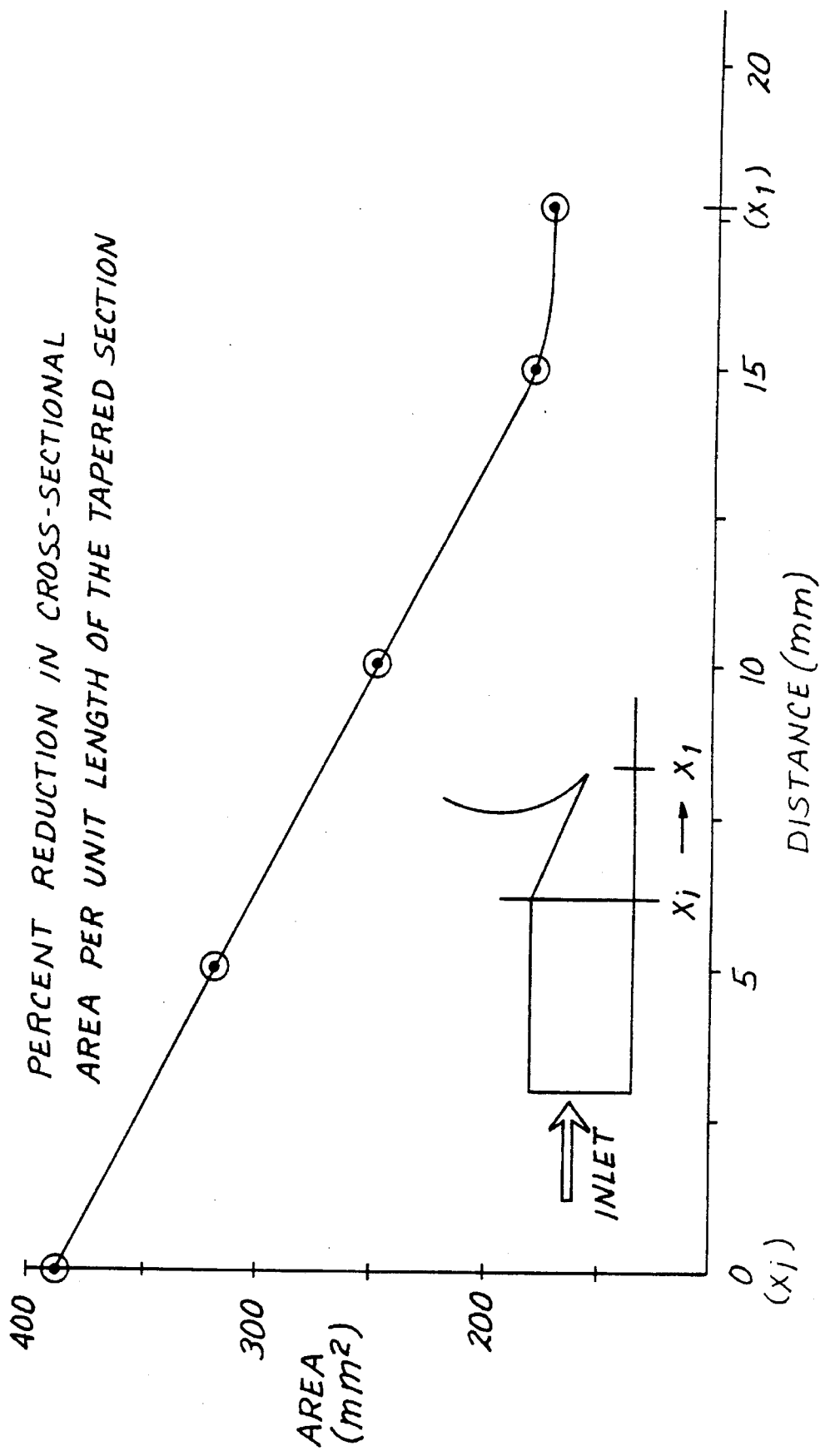
FIG. 10 is a graph of cross-sectional area versus unit length illustrating the reduction in cross-sectional area of the tapered inlet section in accordance with the invention.

FIG. 10 graphically illustrates the reduction in cross-sectional area according to the invention. In the noted embodiment, the initial cross-sectional area of the tapered section 125 (denoted $X_i$) is approximately 380 mm$^2$. At approximately 10.16 mm across the length of the tapered section 125 the cross-sectional area is approximately 245 mm$^2$. At approximately 17.8 mm (denoted $X_t$) a minimum cross-sectional area of approximately 180 mm$^2$ is achieved. Although the change in area of the tapered section 125 is relatively linear per unit length through most of the tapered section, it becomes non-linear close to the throat 126 and, hence, chamber structure 110. In this region, the shape of the cross-section transitions from a substantially circular shape to a substantially elliptical shape (see FIG. 8).

The outlet port 123 of the invention is also designed with a smooth transition from the sac annulus 115. In the preferred embodiment, the outlet port diameter is in the range of 18 to 33 mm, preferably 22 to 23 mm.

In flow visualization studies of the above described inlet and outlet ports 121, 123 it was observed that during pump expansion (i.e., inflow), a uniform, circular flow pattern was produced which acted to evenly wash the interior surfaces of the sac 111. The circular, diastolic flow pattern was very well established and existed until early systole.

The above described inlet and outlet ports 121, 123 are particularly applicable to a deformable sac pump system having a stroke volume in the range of approximately 20 to 70 ml. However, as will be recognized by one skilled in the art, the noted dimensional relationship(s) may, within the scope of the invention, be proportionately scaled up or down to accommodate blood pump systems with higher or lower stroke volumes.

The pump system of the invention also includes inlet and outlet valves to produce one direction flow valving in the pump 100. In the preferred embodiment, the inlet and outlet valves 150, 151 are externally disposed in removable inlet and outlet conduits 160, 161, respectively (see FIG. 4). In further embodiments of the invention (not shown), the inlet and outlet valves may be disposed in the inlet and outlet ports 121, 123.

The removable valved conduits 160, 161 generally comprise externally stented, triple-sinused, tissue-valved polyester conduits with impervious coatings on the external faces of the polyester material (not shown). The conduits 160, 161 are housed in a biocompatible cage 165, which protects the noted structures. The conduits 160, 161 also include a novel means of connecting the device to other blood-carrying components without disruption of smooth blood flow. The connector system also minimizes the number of blood-contacting materials and biomaterial transitions. Further details of the valved conduits are set forth in co-pending application Ser. No. 08/194,481, now U.S. Pat. No. 5,511,958, entitled "Ventricular Assist Device with Valved Blood Conduit and Method of Making", filed Feb. 7, 1994.

As illustrated in FIGS. 4 and 5a, the pump inlet and outlet housings 118, 120 also include connecting means adapted to removably connect conduits 160, 161 to housings 118, 120. According to the invention, the connecting means may include any suitable means to provide a rigid, reliable connection between the inlet and outlet ports 121, 123 and the valved conduits 160, 161.

According to the invention, the connecting means includes sealing means to minimize leakage at the junction between the inlet and outlet ports 121, 123 and the valved conduits 160, 161. In the preferred embodiment, the sealing means comprises at least two substantially concentric seals 181, 182. The concentric seals 181, 182 are described in detail below.

Referring to FIG. 5a, the connecting means includes a housing ring 180 which is secured to the pump bulkhead 188 by suitable means. The ring 180 is preferably formed of a light weight corrosion resistant material such as titanium, or of a strong, rigid fiber composite.

Details of seals 181, 182 will now be considered with particular reference to FIG. 5a. Seal 181 comprises a novel rolled-over sac termination at each respective port opening. More particularly, seal 181 is formed by rolling the sac material over the forward edge of housing ring 180 and securing the sac material to the inner 190 and outer 192 surfaces of the ring 180 by conventional bonding means. The sac material is also mechanically captured or secured to ring 180 by face seal 182 (discussed below) to further enhance the reliability of the connection between the inlet and outlet ports 121, 123 and the valved conduits 160, 161.

As illustrated in FIG. 5a, the rolled-over sac configuration results in a substantially semicircular sealing surface 183 at the port opening. The rolled-over sac configuration also minimizes step transitions, with resulting flow disruption, generally associated with prior art designs.

To further enhance sealing at the pump-conduit 160, 161 interface, a face seal 182 is also employed. The face seal 182 is generally concentric with seal 181 and is secured by suitable means to ring 180 and seal 181. More particularly, face seal 182 is seated within housing ring 180 and is adapted to exert a retaining force against and, hence, secure the sac material to the outer surface 192 of ring 180. According to the invention, the face seal 182 is positioned with the sealing surface of the face seal 184 positioned proximate the parallel plane of sealing surface 183.

As further illustrated in FIG. 5a, the connecting means also includes means to operatively secure the valved conduits 160, 161 to the pump 100. In the preferred embodiment, the housing ring 180 includes threads 186 disposed on the outwardly extending flange 185 which are adapted to engage conduit threads 167. In further embodiments of the invention (not shown), the connecting means may include safety means (e.g., keyed slot(s)) to assure appropriate placement of the inlet and outlet valved conduits 160, 161.

Completing the details of the inlet and outlet connecting means, the pump bulkhead 188 is operatively secured to the pump housing 116 and encases seals 181, 182 and ring 180. The bulkhead 188 may be formed of a light weight, rigid biocompatible material, preferably, polyetheretherketone (PEEK).

As will be recognized by one skilled in the art, the inlet and outlet connecting means of the invention minimizes interposed biomaterials and step transitions. Moreover, the connecting means provides for a direct interface between the pump sac (i.e., polyurethane) and valved conduit (i.e., polyester) without blood-metal contact.

CONTROLS AND EXAMPLES

A series of flow visualization studies were carried out to determine the optimum blood pump inlet and outlet port configuration and size. The studies were conducted on a blood pump system having a stroke volume of 20 to 70 ml.

Figure 11:
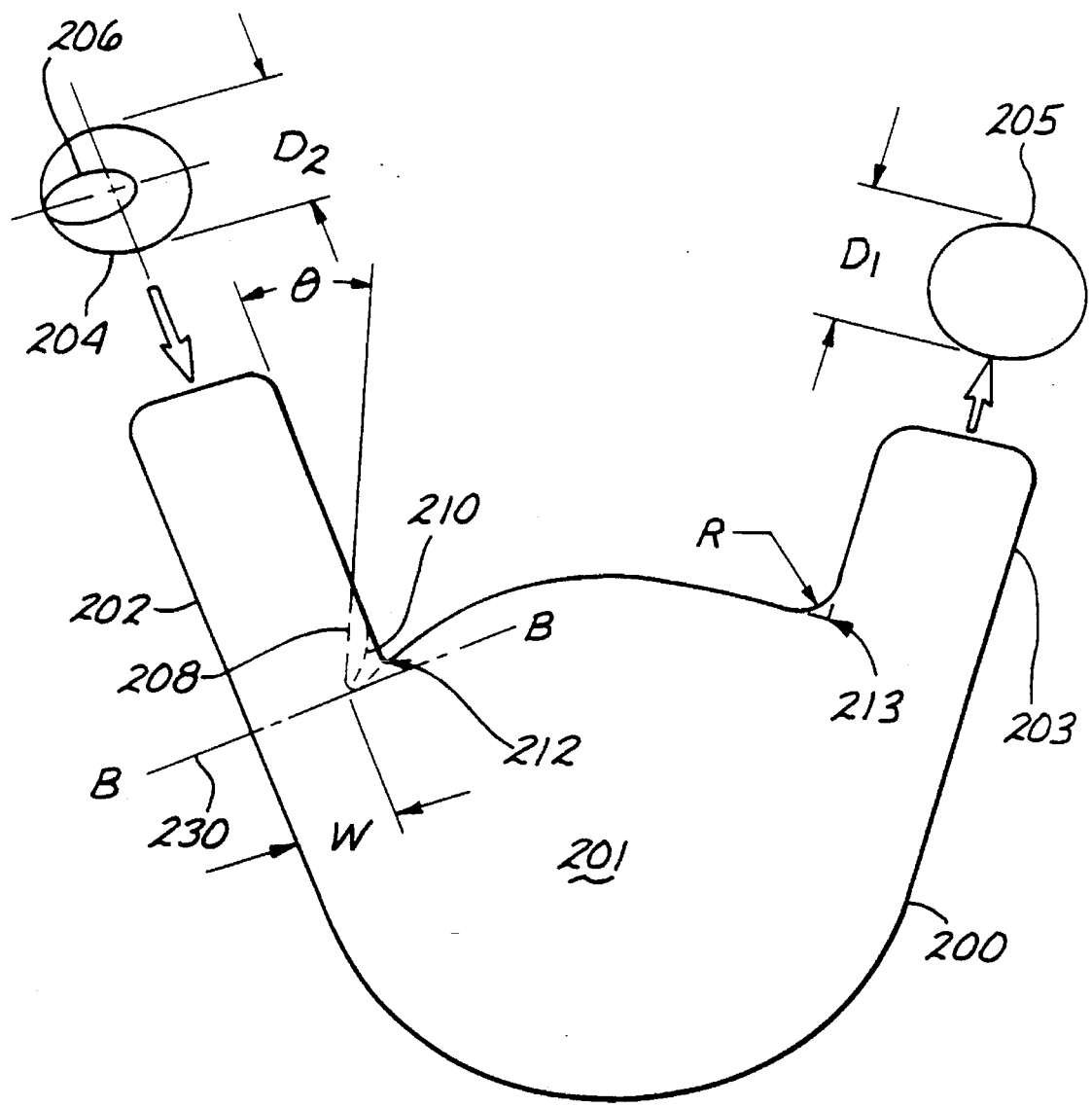
FIG. 11 is a schematic plan view of a blood pump sac illustrating various inlet port configurations.

The blood pump sac which was employed for the flow visualization studies is schematically illustrated in FIG. 11. The sac 200 generally comprises a main sac body or annulus 201 and an inlet and outlet port 202, 203, respectively, having generally circular inlet and outlet openings 204, 205, therein.

The examples which follow illustrate the superior performance of the invention. The examples are for illustrative purposes only and are not meant to limit the scope of the claims in any way.

EXAMPLE 1

In each of the examples the inlet and outlet openings (204, 205) had a generally circular cross-section. The inlet port 202 comprised a straight leg having a diameter ($D_2$) of 20 mm. The outlet port 203 also had a generally circular cross-section with a diameter ($D_1$) of 19.7 mm.

A sharp interface or junction (212) at the inlet port (202) and main sac body (or annulus 201) was employed. The junction (213) at the outlet port (203) and annulus (201) had a radius (R) of 8.4 mm.

With the noted configuration, it was found that the overall flow within the sac was very poor.

EXAMPLE 2

In Example 2 the same outlet configuration and size as Example 1 was employed. However, the inlet port (202) included a straight taper (208) at the inlet/annulus junction. The taper angle ($\theta$) was approx. 17.5°.

The inlet opening (204) had an initial diameter ($D_2$) of 20 mm converging to a generally elliptically shaped throat section (206). The width (W) of the throat section (206) taken along plane B—B, denoted 230 was 16.5 mm and the height (H) was 11.4 to 11.7 mm.

With the noted inlet configuration, fair to good flow characteristics within the pump were observed.

EXAMPLE 3

In Example 3 the same outlet port (203) configuration as Example 1 and 2 was employed. However, the inlet diameter ($D_2$) was changed to 18 mm converging to an elliptically shaped throat (206) having a width (W) of 13.7 and a height (H) of 11.4 to 11.7 mm. The taper angle ($\theta$) was also reduced to 16°.

With the reduced throat width and taper angle, a very good flow pattern within the pump was observed.

EXAMPLE 4

In Example 4 the same outlet (203) configuration and size as Examples 1–3 were employed. A straight taper was employed with a taper angle ($\theta$) of 25° and an inlet diameter ($D_2$) of 22 mm converging to a throat width (W) of 12.7 mm.

The above noted configuration also resulted in a very good flow pattern within the pump. However, this configuration was found to be too restrictive.

EXAMPLE 5

In Example 5 the same inlet and outlet configuration and size as Example 4 were employed, with the exception that the taper angle ($\theta$) was 22° and the throat width (W) was 14.5 mm.

The flow pattern observed with this configuration was also very good.

EXAMPLE 6

In Example 6 the same inlet and outlet configuration and size as Example 5 were employed. However, a radiused taper (210) was employed.

With the radiused taper it was found that the flow pattern within the pump was not as good as the straight tapered inlet. It was further found that the noted inlet configuration was too restrictive.

EXAMPLE 7

In Example 7 the same inlet and outlet port (202, 203) configurations as Example 5 were employed. However, due to the requirement for a tapered inlet (208) and the noted dimensional tolerances, it became necessary to enlarge the outlet diameter ($D_1$) in order to allow for the removal of the sac 200 from the mandrel during manufacturing. It was estimated that the minimum "removable" diameter would be approximately 25 mm. A new mandrel was thus designed to produce a sac with a tapered inlet port (202) ($\theta=26°$) and a 25 mm diameter outlet (203). A radius (R) of 9.7 mm at the junction (213) of the outlet and annulus was also employed.

Although the flow pattern observed with the above noted configuration was good to very good, it was found that the larger outlet acted as an extension of the main chamber (201) resulting in generally slower flow in the chamber. The vortex formation in the main chamber (201) was also slower than in Example 5.

EXAMPLE 8

In Example 8 the same inlet port configuration and size as Example 7 were employed. The same outlet port configuration as Example 7 was also employed, with the exception that the outlet diameter ($D_1$) was reduced to 24 mm and a sharp interface at the outlet/annulus junction (213) was employed.

With the above noted dimensions, the resulting flow pattern was found to be very good, but not as good as Example 7.

EXAMPLE 9

In Example 9 the same inlet configuration as Example 8 was employed. The outlet port configuration of Example 8 was employed, with the outlet diameter ($D_1$) reduced to 23 mm.

It was found that reducing the outlet diameter 1 mm resulted in an excellent flow pattern throughout the pump. On the basis of this experiment, it was determined that the maximum outlet diameter was 23 mm.

EXAMPLE 10

In Example 10 the same inlet port configuration and size as Example 9 was employed. However the outlet diameter ($D_1$) was further reduced to 22 mm and a radius (R) of 6.4 mm was employed at the outlet/annulus junction (213). The 6.4 mm radius was employed to facilitate removal of the sac from the mandrel during manufacturing.

With the above noted dimensions, an optimum flow pattern was observed within the pump.

A summary of the above experimental results is set forth in Table I.

It may be seen, therefore, that the present invention provides a blood pump system for internal use in humans or animals and which is particularly suited for use as a left ventricular assist device. The system provides for removable inlet and outlet conducts having valves therein. The novel inlet configuration also results in smooth transition areas on all internal surfaces. Moreover, sites for thrombus formation are minimized and a smooth circular flow with even washing of all pump surfaces results.

Various modifications of the invention will become apparent to those skilled in the art from the foregoing description and accompanying drawings. Such modifications are intended to fall within the scope of the appended claims.

TABLE I

| Example No. | PUMP CONFIGURATION | | Flow Result |
|---|---|---|---|
| | Inlet | Outlet | |
| 1 | $D_2$ = 20 mm<br>Sharp interface | $D_1$ = 19.7 mm<br>R = 8.4 mm | Very poor |
| 2 | $D_2$ = 20 mm<br>Straight taper:<br>W = 16.5<br>H = 11.4–11.7 mm<br>θ = 17.5° | $D_1$ = 19.7 mm<br>R = 8.4 mm | Fair to good |
| 3 | $D_2$ = 18 mm<br>Straight taper:<br>W = 13.7<br>H = 11.4–11.7 mm<br>θ = 16° | $D_1$ = 19.7 mm<br>R = 8.4 mm | Very good |
| 4 | $D_2$ = 22 mm<br>Straight taper:<br>W = 12.7<br>H = 11.4–11.7 mm<br>θ = 25° | $D_1$ = 19.7 mm<br>R = 8.4 mm | Very good |
| 5 | $D_2$ = 22 mm<br>Straight taper:<br>W = 14.5<br>H = 11.4–11.7 mm<br>θ = 22° | $D_1$ = 19.7 mm<br>R = 8.4 mm | Very good |
| 6 | $D_2$ = 22 mm<br>Radiused taper:<br>W = 14.5<br>H = 11.4–11.7 mm | $D_1$ = 19.7 mm<br>R = 8.4 mm | Good-slow vortex formation |
| 7 | $D_2$ = 22 mm<br>Straight taper:<br>W = 14.5<br>H = 11.4–11.7 mm<br>θ = 26° | $D_1$ = 25 mm<br>R = 9.7 mm | Good-very good |
| 8 | $D_2$ = 22 mm<br>Straight taper:<br>W = 14.5<br>H = 11.4–11.7 mm<br>θ = 26° | $D_1$ = 24 mm<br>Sharp interface | Good-very good |
| 9 | $D_2$ = 22 mm<br>Straight taper:<br>W = 14.5<br>H = 11.4–11.7 mm<br>θ = 26° | $D_1$ = 23 mm<br>Sharp interface | Excellent |
| 10 | $D_2$ = 22 mm<br>Straight taper:<br>W = 14.5<br>H = 11.4–11.7 mm<br>θ = 26° | $D_1$ = 22 mm<br>R = 6.4 mm | Excellent |

What is claimed is:

1. A blood pump system for internal use in humans, comprising:

a deformable sac, said sac having in the non-deformed configuration a pair of opposite substantially parallel and planar walls of substantially circular shape joined by an annular wall of substantially semi-circular cross-section, said sac being formed in a seamless piece of flexible resilient material, said sac including inlet and outlet means extending from said annular wall of said sac substantially tangentially with respect to said annular wall;

a pair of plates disposed on opposite sides of said sac, each of said plates being engageable with a respective one of said planar walls of said sac for displacing at least one of said planar walls toward the other to deform said sac;

inlet conduit means removably connected to said inlet means including valve means for controlling inlet flow;

first connecting means for operatively connecting said inlet conduit means to said inlet means, said first connecting means including first sealing means for sealing said inlet conduit means and said inlet means connection, said first sealing means comprising at least two substantially concentric annular seals, one of said seals comprising a semi-circular surface formed by rolling said sac over a portion of said first connecting means, another of said seals contacting and retaining said sac against said portion;

outlet conduit means removably connected to said outlet means including valve means for controlling outlet flow; and second connecting means for operatively connecting said outlet means, said second connecting means including second sealing means for sealing said outlet conduit means and said outlet means connection, said second sealing means comprising at least two substantially concentric annular seals, one of said seals comprising a semi-circular surface formed by rolling said sac over a portion of said second connecting means, another of said seals contacting and retaining said sac against said portion.

2. The blood pump system of claim 1, further comprising:

bonding means for securing said sac to said portion of said first connecting means.

3. The blood pump system of claim 1, further comprising:

bonding means for securing said sac to said portion of said second connecting means.

* * * * *